United States Patent
Francis (10) Patent No.: US 6,488,036 B1
(45) Date of Patent: *Dec. 3, 2002

(54) DENTAL FLOSS DISPENSER AND METHOD

(76) Inventor: Shlomo Francis, 6604 N. Richmond St., Chicago, IL (US) 60645

( * ) Notice: Subject to any disclaimer, the term of this patent is extended or adjusted under 35 U.S.C. 154(b) by 0 days.

This patent is subject to a terminal disclaimer.

(21) Appl. No.: 09/432,493

(22) Filed: Nov. 2, 1999

(51) Int. Cl.[7] .............................................. A61C 15/00
(52) U.S. Cl. ...................... 132/325; 132/324; 132/326; 132/327
(58) Field of Search ................................ 132/323, 324, 132/325, 326, 327, 328, 329

(56) References Cited

U.S. PATENT DOCUMENTS

| | | | |
|---|---|---|---|
| 911,664 A | 2/1909 | Locke | |
| 2,554,526 A | 5/1951 | Dembenski | 132/92 |
| 2,931,371 A | 4/1960 | Petitta | |
| 3,870,059 A | 3/1975 | Bennington | 132/92 |
| 3,896,824 A | 7/1975 | Thornton | 132/92 |
| 4,326,547 A | 4/1982 | Verplank | 132/89 |
| 4,364,380 A | 12/1982 | Lewis | 128/89 |
| 4,637,412 A | 1/1987 | Martinez | 132/92 |
| 4,657,034 A | 4/1987 | Koski | 132/92 |
| 4,974,614 A | 12/1990 | Selker | 132/321 |
| 5,050,625 A | 9/1991 | Siekmann | 132/323 |
| 5,052,420 A | 10/1991 | Chen | 132/325 |
| 5,094,255 A | 3/1992 | Ringle | 132/321 |
| 5,101,843 A | 4/1992 | Peng | 132/323 |
| 5,176,157 A | 1/1993 | Mazza | 132/322 |
| 5,184,631 A | 2/1993 | Ikeda | 132/323 |
| 5,199,452 A | 4/1993 | Cheng | 132/325 |
| 5,224,502 A | 7/1993 | Walker, Jr. | 132/325 |
| 5,289,836 A | 3/1994 | Peng | |
| 5,415,188 A | 5/1995 | Altshuler | 132/325 |
| 5,573,022 A | 11/1996 | Winters | 132/325 |
| 5,613,508 A | 3/1997 | Bushman | 132/325 |
| 5,899,214 A | 5/1999 | Francis | 132/323 |

OTHER PUBLICATIONS

Flosspopper™ Instructions, GAG International, Inc. Mar. 1995.

*Primary Examiner*—John J. Wilson
*Assistant Examiner*—Robyn Kieu Doan
(74) *Attorney, Agent, or Firm*—Brinks Hofer Gilson & Lione (57) ABSTRACT

A single support dental flosser with improved maneuverability; to provide the user with increased leverage and dexterity to easily and thoroughly clean food, debris, and dental plaque so as to prevent proximal caries and periodontal disease. The dental flosser includes a handle section, an intermediate section, and an upstanding dental floss support section. In an embodiment of the invention, the dental flosser includes a preset strand of floss attached to the upstanding dental floss support section. In an other embodiment, the dental flosser includes a main body portion having a cylindrical shape for ease of handling. A hollow interior containing a metered floss dispenser, and a floss support containing a through hole to supply floss. The metered floss dispenser has a simplified construction and is especially designed to fit into a cylindrically shaped handle. The floss support is slender to deem the device suitable for use by orthodontic patients where the maneuverability is especially crucial to allow thorough cleaning under orthodontic appliances.

30 Claims, 5 Drawing Sheets

DENTAL FLOSS DISPENSER AND METHOD

BACKGROUND OF THE INVENTION

The present invention relates to easily maneuvered dental flossing devices and methods of flossing teeth using the same. More particularly it relates to single posted dental flossing devices with improved maneuverability including assemblies for metered floss dispention which are capable of being contained in such dental flossing devices and slender floss supports which allow the use of such dental flossing devices in orthodontic patients.

A dental flosser is used in such a manner that the dental floss is intruded between the adjacent surfaces of two teeth and into the gingival sulcus and then the floss is urged to scrape the surfaces to dislodge and remove food debris and dental plaque. The dental flosser appears to be a most effective tool for cleaning the adjacent surfaces of the teeth in cooperation with the toothbrush. While many prior art devices contain, dispense, and support dental floss in one way or another, they nevertheless suffer from a number of significant shortcomings and drawbacks. In particular, such prior art devices are restrictive in the manipulative sense, and thus awkward to use. They fail to protect the gums from injury. They do not permit easy disengagement or repositioning upon breaking or sticking of floss between teeth. They do not permit simple releasing and locking of dental floss. Also they suspend the floss in a fixed position between two floss supports and therefore fail to fully exploit the strength, flexibility affordable by the human hand. Furthermore, during the orthodontic treatment period, a fixed orthodontic appliance is applied to the patient and a metal orthodontic wire is fixed between the teeth so that the conventional flosser is unable to go between the teeth to perform the up and down, left and right scraping movement. In addition, the conventional dental flosser is not designed to accommodate the requirements of a patient under orthodontic treatment. The excessively thick floss supports cannot fit through the quite narrow clearance between the metal orthodontic wire and the adjacent surface of the teeth. (The clearance between the metal orthodontic wire and the adjacent surface of the teeth is referred hereinafter as "clearance.")

Attempts to provide dental flossers that are suitable for orthodontic patients have generally produced dental flossers that include two floss supports and a I strand of floss suspended between them. This frees the user from the necessity of grasping the floss with his fingers, but has the decided disadvantage of restricting maneuverability within the clearance. All of the prior art had to be moved as one inflexible unit. The one post and a flexible floss design provide increased maneuverability and access within the clearance.

For example, U.S. Pat. No. 5,101,843 to Peng, and U.S. Pat. No. 5,184,631 to Ikeda and the FLOSSPOPPER brand dental flosser, which is distributed by GAC, all disclose dental flossers of the two-post design. This design suffers from a number of disadvantages:

(a) Since the prior art is maneuvered as one inflexible unit, it does not allow vertiginous maneuvering within the clearance. This limitation increases difficulty and decreases cleaning efficiency of flossing.

(b) An inflexible unit does not permit varying the degree of tautness of the floss. Tautly pulled floss injures gums more readily than gently suspended floss that can respond to the variable surface of the gum line. Indirectly applying pressure to the floss, through the floss supports decreases control over the force and extent of insertion of the floss further increasing the risk of injury to the gums.

(c) When the floss is suspended between two posts, one cannot exert maximum pressure to the floss because pressure is indirectly applied via the supports. This decreases the efficiency of its cleaning power.

(d) Since the prior-art flosser is maneuvered as one inflexible unit, it requires increased dexterity to properly insert the flosser into the tiny clearance, and at the same time concentrate on properly intruding the floss between the adjacent surfaces of two teeth. The increased time and effort can discourage the user from flossing as often and as thoroughly as desired.

(e) Since the prior art is maneuvered as one inflexible unit, it requires inordinate perseverance to clean the back teeth at the necessary 90 degree angle as the mouth does not open wide enough for proper access.

(f) The dexterity required to properly floss with prior art devices is beyond the capability of many juveniles who comprise the majority of orthodontic patients.

(g) The prior art makes no provision for replacing floss, so the entire apparatus must be disposed of after use, which measurably increases cost.

While the FLOSSPOPPER has the other disadvantages of the two-post flosser, it is not disposable. However, the floss must be threaded into several cavities prior to each use. Furthermore, plaque can accumulate within the cavity, thereby obstructing future re-threading. Furthermore, there is no locking mechanism for the floss, which must be grasped manually during the entire flossing process. It is extremely difficult to maintain one's grip on the floss when teeth are tightly wedged; therefore, floss often requires repeated re-threading.

SUMMARY OF THE INVENTION

In an embodiment of the present invention there is provided a single post flossing device that comprises a body portion having a thickness and a length and having a first end and a second end, an intermediate housing portion having a thickness and a length and having a first end and a second end; a slender post portion having a thickness and a length and having a first end and a second end and a floss portion having a thickness and a length and having a first end and a second end. In this embodiment the second end of the body portion is attached to the first end of the intermediate housing portion, the first end of the slender post portion is attached to the intermediate housing, the first end of the floss portion is adjacent and fixed to the second end of the slender post portion, and the second end of the floss portion being free from attachment to the device. In this embodiment, the thickness of the slender post portion is substantially thinner than the thickness of the body portion and the intermediate housing portion.

In additional embodiments the thickness of at least part of the slender post portion may be thin enough to allow insertion of the post into a clearance between the teeth to be flossed and a fixed orthodontic appliance. In additional embodiments of this embodiment, at least part of the post is thin enough to allow the user to maneuver the post inside the clearance. More preferably, wherein at least part of the post is thin enough or substantially cylindrical to allow the user laterally rotate the device to orientation favorable to the user after insertion into the clearance thereby rotating the needle without obstruction by the fixed orthodontic appliance, and further allowing the user to maneuver the post inside the clearance while the device is positioned in those orientations. Still more preferably wherein at least part of the post is thin enough or substantially cylindrical to allow the user to laterally rotate the device to a variety of orientations and insert the post into the clearance at those orientations thereby allowing the entire flossing motion to be executed from a position most favorable to the user. The slender post may comprise a twisted wire strand, having a loop or a through-hole at the second end of the strand, the first end of floss being fixed in the through-hole. Preferably the wire strand should be thin at an intermediate section and wider at the top thereby forming a slender post which is easy to maneuver and a widened loop which is easy to thread and gentle to the gums.

In further embodiments of the present invention the intermediate housing may comprises a wall, an opening in the wall, a spool of floss, and have the floss extending through the opening and being removable attached and fixed to the second end of the slender post portion. The single post-flossing device may have a slender post wherein the thickness of the slender post is not greater than about 1 mm, is not greater than about 1.5 mm, is not greater than 3 mm, and is not greater than 5 mm.

In an other embodiment of the present invention there is provided a disposable single post flossing device comprising: a body portion having a thickness and a length and having a first end and a second end; a slender post portion having a thickness and a length and having a first end and a second end; a floss portion having a thickness and a length and having a first end and a second end; the second end of the body portion being rigidly attached to the first end of the slender post portion; the first end of the floss portion being permanently fixed to the second end of the slender post portion, and the second end of the floss portion being free from attachment to the device; and, the thickness of the slender post portion being thinner than the thickness of the body portion and the thickness of the slender post portion at the area where the floss is attached being thinner than about 5 mm. In additional embodiments of this embodiment the thickness of the post is not greater than about 5 mm, is not greater than 3 mm, and is not greater than 1 mm.

In another embodiment of the present invention the single post flossing device comprises a slender post portion having a first and a second end portion and which comprises a twisted wire strand; the twisted wire strand having a loop at the second end of the post; the first end of the floss being permanently fixed in the loop.

In yet a further embodiment of the present invention there is provided a disposable single post flossing device in which the first end portion of the slender post portion is removably attached to the body portion of the device.

In another embodiment of the present invention there is provided a method of flossing using a single post flossing device for an individual having orthodontics which method comprises: providing a length of floss having a first end and a second end, a post having a first end and a second end and the first end of the floss being fixed to the second end of the post; inserting the second end of the post and attached floss between the space between the orthodontics and the teeth and gums and position the floss between the teeth; moving the floss, in a flossing action, along the teeth and gums; and, maintaining the second end of the post portion in the space between the orthodontics and the teeth and gums during at least a portion of the flossing movement.

In a further embodiment of the present invention there is provided a dental flossing device comprising a main housing having a dental floss supporting portion, a handle portion, and a hollow interior for containing a reel of dental floss interiorly therein; a reel of dental floss; a disengageable locking mechanism for preventing the rotation of said dental floss reel; and, at least part of said reel having a substantially cylindrical shape with a diametric extent only slightly larger than the diametric extent of said part of said reel being telescopingly mounted inside said hollow interior for allowing rotational motion to said reel when said locking mechanism is disengaged. This device may further have the reel of floss and locking mechanism mounted in the interior of said handle portion and wherein said handle portion is of a substantially hollow cylindrical shape for case of grasping and economy of manufacture. This device may still further have a locking mechanism that further comprises a ratchet comprising a cantilevered arm having a free end, said free and having a detent for engagement with at least one tooth.

In yet still another embodiment of the present invention there is provide a method of flossing using a single support flossing devise comprising: providing a length of floss having a first end and a second end, a support wing; having a first end a second end, and the first end of the support being fixed to the main body portion with a section of the main body protruding in a direction perpendicular to said support; and said first floss being fixed to said second of the support in a manner allowing the floss to be suspended in a plurality of direction; grasping said body portion in one hand; using the second hand to suspend the floss; inserting the floss into the mouth; positioning the floss between the teeth; utilizing the length of the support to urge the floss upwardly between the teeth; rotating said body portion to a position most favorable to user and adjusting the position as necessary during the flossing of the teeth; and, tilting said support to urge the floss to clean the convex surface of the teeth.

OBJECTS OF THE INVENTION

It is the object of the present invention to provide a flexible flosser with unrestricted maneuverability within the clearance, providing easier insertion and increased cleaning efficiency of flossing.

It is a further object of the invention to provide a flosser, which has fastened to it only one end of floss allowing the second end of floss to be grasped by the user or any other non-integral means. As in such a device, the user can intrude the floss between the teeth by alternately applying pressure to opposite sides of the floss thereby regulating the force and extent of the insertion.

It is a further object of the invention to provide a flosser with improved flossing efficiency by allowing the finger to direct the pressure.

It is a further object of the invention to provide a flosser where the floss can be adjusted to varying degrees of tautness, as loosely suspended floss can respond to the variable surface of the gum line, thereby minimizing risk of injury to the gums.

It is a further object of this-invention to provide a flosser, which requires decreased time and effort to use and will encourage thorough and frequent cleaning. The present invention further has as its object to provide a flosser that is easily maneuvered by juveniles, even to the back teeth.

It is the further object of the invention to provide a flosser in which clean floss can be easily accessible during flossing.

It is the further object of the invention to provide a simple and economical locking dispenser for ease of use and economy of manufacture.

It is the further object of the invention to provide an economical, nondisposable, continuously feeding, metered and locking floss dispenser and applicator that eliminates the need for constant re-threading. Further objects and advantages of my invention will become apparent from a consideration of the drawings and ensuing description.

DETAILED DESCRIPTION OF PREFERRED EMBODIMENT

Figure 5:
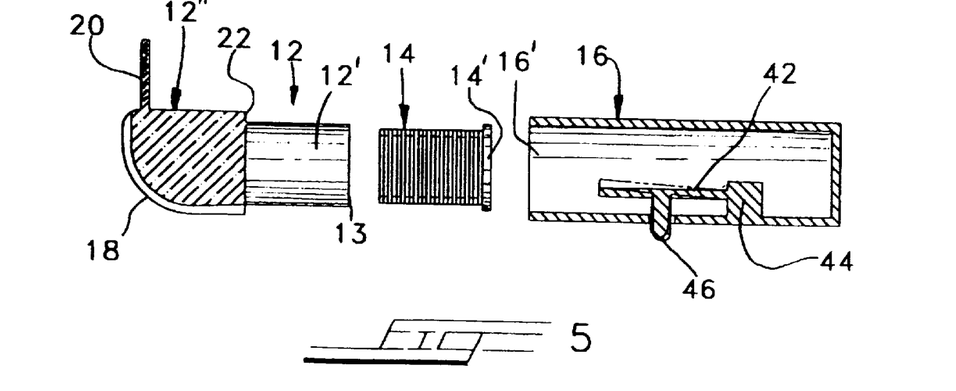
FIG. 5 is an assembly view, in cross section.

Referring now to the drawings, there is shown an embodiment of a dental flosser. The dental flosser maybe made up of three main components, as best seen in FIG. 5: A first, dental-floss mounting and dispensing section 12, a dental-floss supply or reel 14, and a second, outer main cover or housing section 16. The first section 12 defines a substantially cylindrically-shaped, partially-hollow interior portion 12' in which the supply of dental floss 14 is received, and also defines another forwardly-located portion 12" having a smooth, curved lower outer surface 18 against which the exiting dental floss contacts during dispensing. I Projecting from the upper surface of the first section is a single, upstanding floss-receiving post 20.

Figure 6:
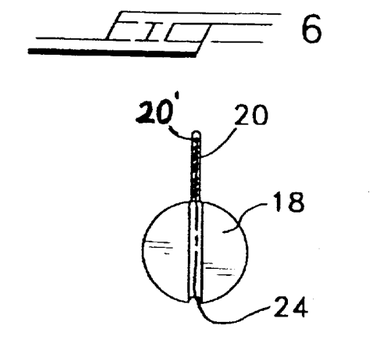
FIG. 6 is a left end view of FIG. 4.

The post 20 is preferably made of twisted wire as best shown in FIG. 6. The wire is made to form a loop or a through-hole 20' and can be coated with various materials to prevent injury to gums. Other structures and materials can be used, to form the post 20 also the post 20 and the first section 12 can be formed from a single and unitary plastic material part. The post 20 should be of enough strength to allow the user to exert pressure on the floss via the post 20. The post 20 should be slender, under 1 mm and even under 5 mm. The thickness of the post may range from about 2 to about 5 mm, it may be less than about 5 mm, less than about 3 mm, and less than about 2 mm. Additionally, the post maybe slightly wider at the tip to form an easily maneuvered post which is safer for the gums and allows easy threading of the through-hole. The support 20 should preferably be of sufficient length to allow easy insertion into the clearance but not overly long as to the risk of injury to the gums, even more preferably between 0.25 inches and 0.30 inches.

The portion 12' has a smaller diametric extent than the portion 12" to define an annular shoulder 22 against which the end 16' of the housing section 16 abuts when the device 10 is fully assembled. The exterior diameter of the portion 12' is less than the interior diameter of the housing section 16, so that the housing section is partially telescopingly-mounted about the portion 12' in a manner that allows the thread to exit and be dispensed in the annular volume between the exterior surface of the portion 12' and the interior surface of the housing section 16, in the manner described hereinbelow. The outer surface 18 of the forwardly-located portion 12" is provided with an elongated, longitudinally-extending groove or channel 24, as best seen in FIG. 6, in which runs the dental floss as it approaches the single post 20. As the dental floss is dispensed, or unwound from the supply reel 14, it exits from the open end of the interior portion 12', and travels along the groove 24 and passes through the opening 20' of the post 20. The depth of the groove 24 is such that the bottom section thereof is coextensive with the lower annular volume defined between the interior annular wall of the housing section 16 and the exterior surface of the section 12', so that the floss may pass unobstructed from the reel to the groove. There also may be provided a cutout on the end-edge 13 of the section 12 through which the floss may pass on its way to the groove 24, so that sharp turns and edges may be obviated in order to prevent the inadvertent cutting of the floss.

Figure 4:
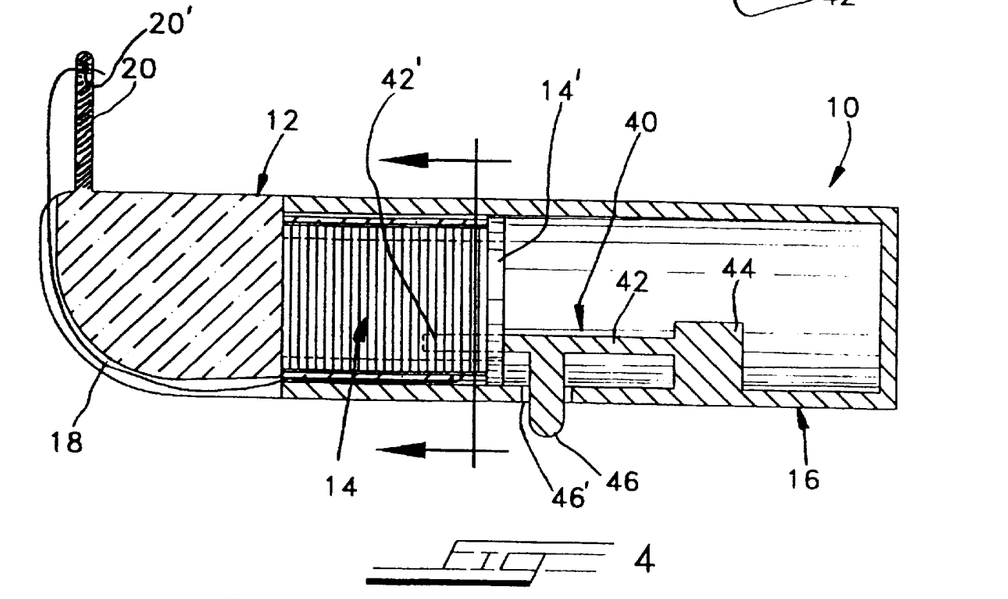
FIG. 4 is a longitudinal cross-sectional view of FIG. 1.
Figure 7:
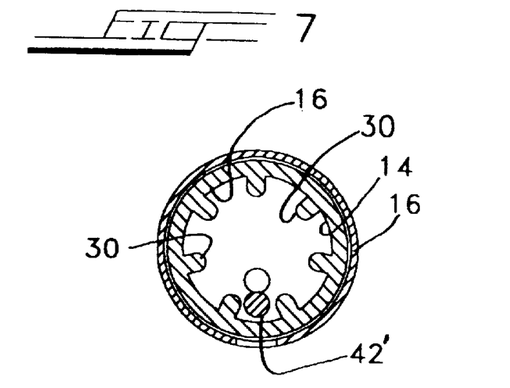
FIG. 7 is a cross-sectional view taken along line 7—7 of FIG. 4.

Mounted within the portion 12' is the dental floss supply or reel 14. This supply may be in reel or other form, and is preferably held therein to allow for rotational movement as the dental floss is dispensed. The reel 14 is a simple spool, or the like, about which the floss is wound, although other structures may be used, or just a simple ball of the floss may be used with a reel, as long as the ball is allowed adequate movement during dispensing. The reel 14 has a hollow interior and an annular end-flange 14'. The end-flange has a greater diametric extent than the main body of the reel or spool 14, which outer diameter is approximately equal to the inner diameter of the housing section 16, as best seen in FIG. 4, so as to provide a friction-fit between the outer surface of the end-flange 14' and the inner surface of the housing section 16. This force-fit allows the housing section to be retained in place when using the device, yet allows for easy opening of the device by sliding the housing section 16 away from the first section 12, in order to allow for replacing the reel 14. Other conventional structure may be used for achieving the releasable connection between the outer housing and the portion 12'. The reel 14 is provided interiorly thereof with a plurality of detents or protuberances 30, there being, for example, seven such detents, as seen in FIG. 7, although more ₁or less may be used, which together form a ratchet wheel. The detents 30 are equi-angularly spaced apart and project from the inner surface of the reel 14. The detents 30 are used to prevent rotation of the reel 14 when the device is being used to floss the teeth by means of a pawl mechanism 40 mounted in the interior of the housing section 16. The pawl-mechanism 16 is comprised of an elongated, resilient lever-arm 42 anchored to the interior of the housing section 16 by means of an anchor or post 44. The arm 42 may be made of resilient thermoplastic material, or other, well-known flexible material that allows the pivotal movement of the arm relative to the anchor 44. The lever-arm 42 extends a great enough distance parallel to the longitudinal axis of the housing section 16 so as to protrude into the interior of the reel 14, as seen in FIG. 4. Protruding from a mid-section of the lever-arm 42 is a button or projection 46 that protrudes outwardly from the interior of the interior of the housing section 16 by means of a hole or opening 46' provided in the housing section. When the device 10 is being used to floss the teeth, the lever-arm is positioned as shown in FIG. 4, with the button 46 protruding fully outwardly through the hole 46', and with the end 42' of the lever-arm 42 being located between,two adjoining detents 30 of the interior of the reel, as seen in FIG. 7, whereby rotation of the reel is prevented. When new floss is to be dispensed, one simply depresses the button 46 inwardly to force the lever-arm 42 more interiorly into the housing section, which thereby displaces the end 42' to a region that does not intersect with the detents 30, whereby free rotation of the reel is allowed in order to dispense the floss.

Figures 1, 3:
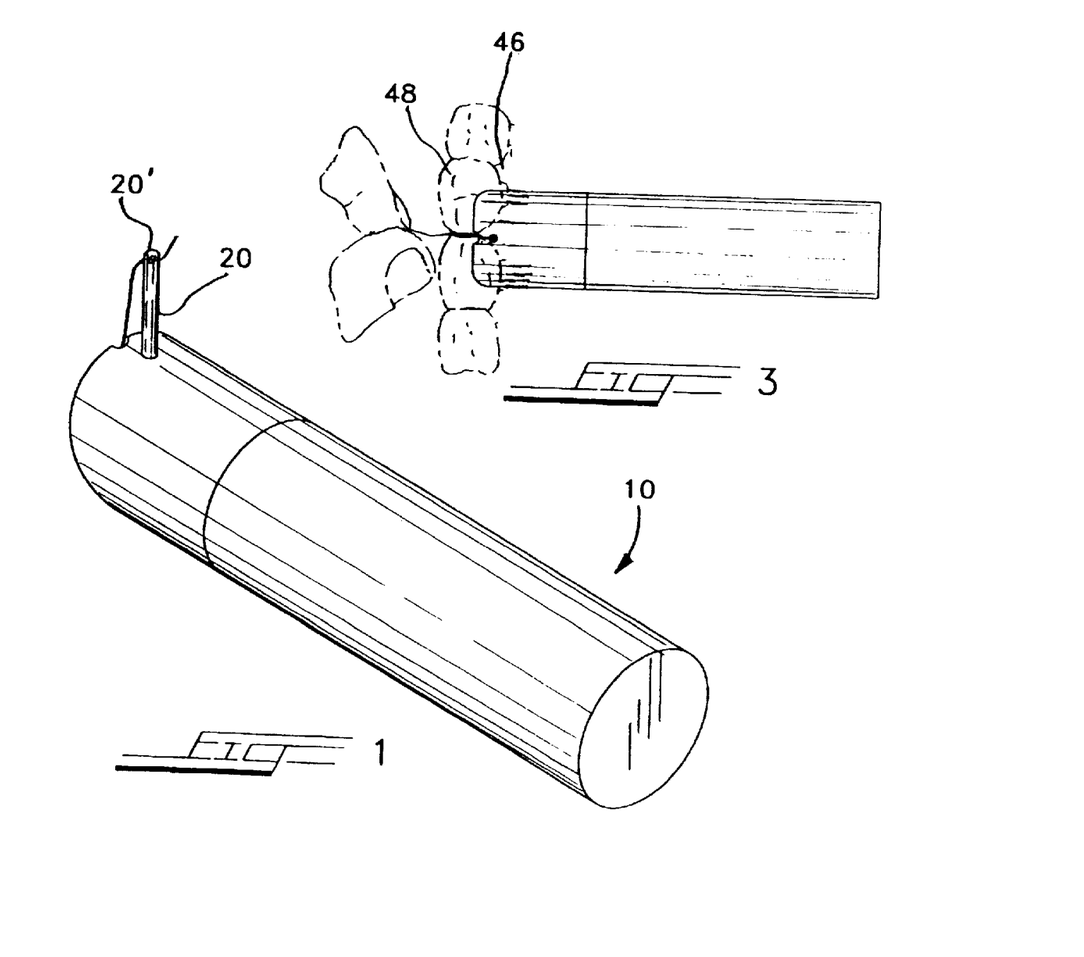
FIG. 1 is a perspective view of an embodiment of the invention containing a strand of dental floss therein.
FIG. 3 is a top view of FIG. 2.
Figure 2:
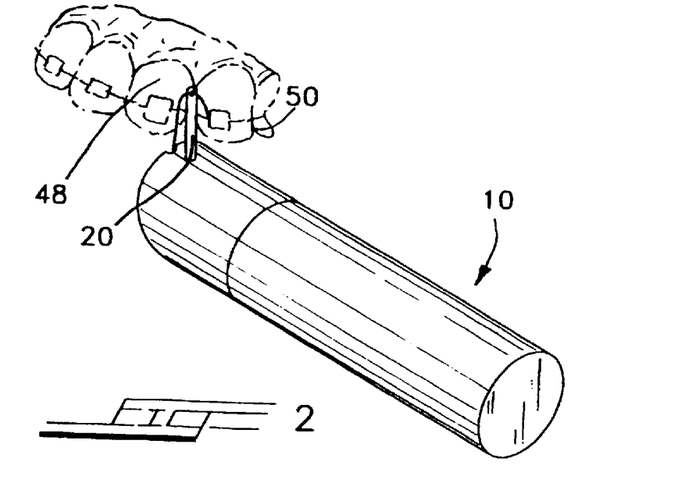
FIG. 2 is a perspective view thereof showing the single post of the dental flosser of an embodiment of the invention in use for flossing teeth.

FIGS. 2 and 3 show the device 10 in working position. The user is to grasp the loose end of floss with his finger. However; a non-integral device suitable for grasping floss may also be used. The floss support or post 20 can then be inserted into the clearance 46 between the teeth 48. The dental floss is then intruded ! between the adjacent surfaces of the two teeth by alternating pressure between the two ends of the floss. Clean floss is easily dispensed during flossing by pressing the button 40.

Figure 8:
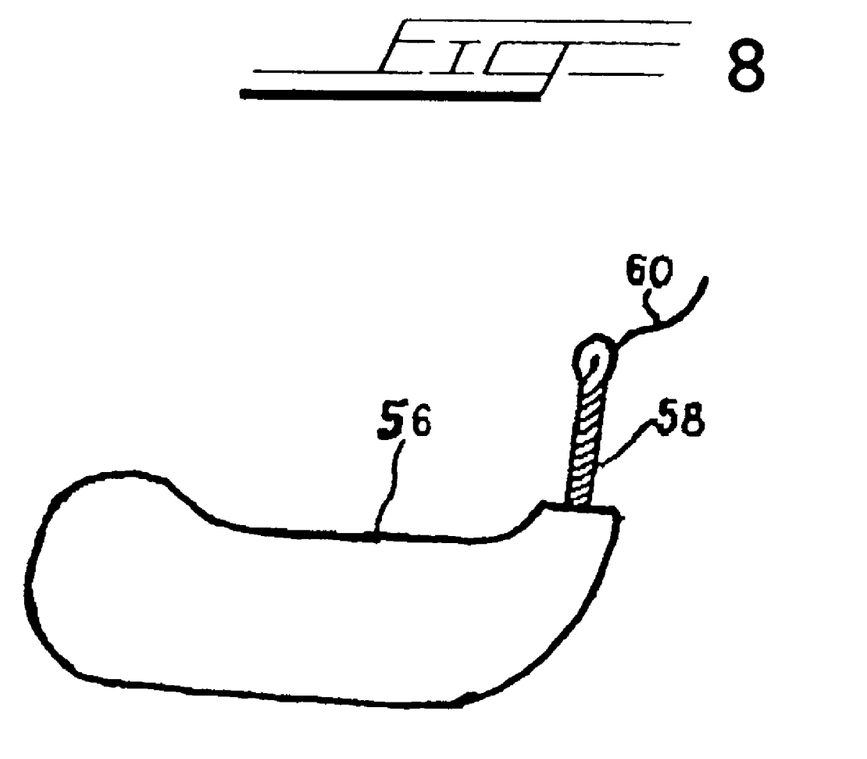
FIG. 8 is a side view of an embodiment of the present invention.

As illustrated in FIG. 8, another embodiment of the dental flossing device comprises a main body portion 56. Projecting from the upper surface of the main body portion is a single, upstanding dental floss support post 58. Held in the top of the post 58, is a strand of floss 60 that may be precut. The floss may be clamped, crimped, tighten, tied, glued, or secured to the post by any other methods and materials known to the art. The floss may be permanently, semi-permanently or removably attached to the post. The post can be coated with various materials to prevent injury to the gums and to aid in the fastening of the floss 60. Other structures and materials can be used to form the post 58, also the post 58 and the body portion can be molded from a single and unitary plastic material part. Furthermore, the floss can be molded into the post at the time when the post is made. The post 58 should be of enough strength to allow the user to exert pressure on the floss via the post 58. The post 58 should be slender, from 1 to 15 mm, under about 3 mm under about 2 mm, preferably under 1.5 mm even more preferably about 1 mm and it may be slightly wider at the tip for an easily maneuvered post which is safe for the gums and allows easy threading of the through hole. The post 58 should preferably be of sufficient length to allow easy insertion into the clearance but not overly long so as to increase the risk of injury to the gums, even more preferably between 0.25 inches and 0.30 inches.

Since the end of the floss is held by the user, the amount of tension applied to the floss may be varied at all times during the flossing. Furthermore, the end of the floss may be maneuvered to any desired orientation that more efficiently effects the flossing of the teeth, which the prior-art devices with two fixed, posts cannot achieve.

Figure 12:
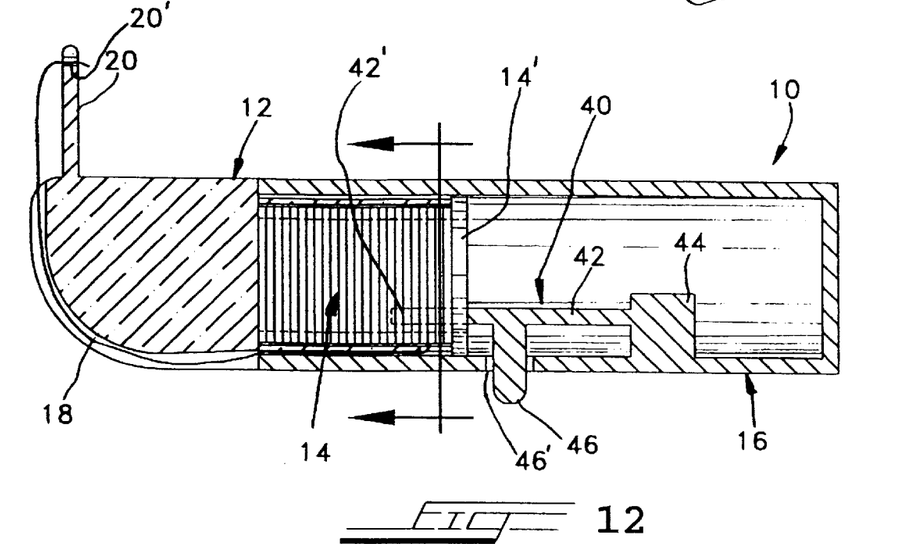
FIG. 12 is a longitudinal cross-sectional view of FIG. 9.
Figure 13:
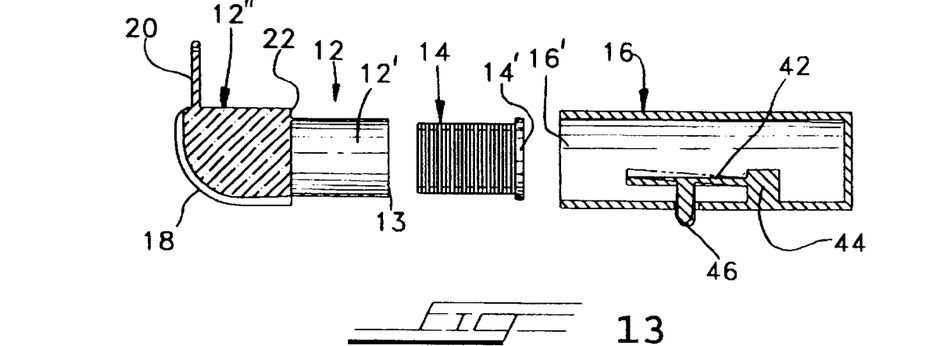
FIG. 13 is an assembly view, in cross section.
Figure 14:
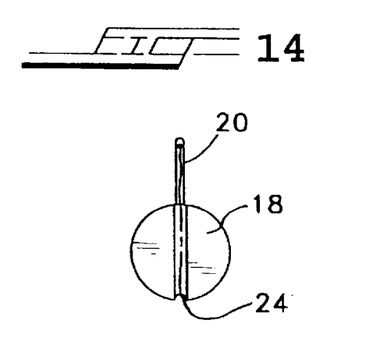
FIG. 14 is a left view of FIG. 12.

Referring now to the drawings FIGS. 9–13, there is shown another dental flosser 10. The dental flosser is made up of three main components, as best seen in FIG. 13: A first, dental-floss mounting and dispensing section 12, a dental-floss supply or reel 14, and a second, outer main cover or housing section 16. The first section 12 defines a substantially cylindrically-shaped, partially-hollow interior portion 12' in which the supply of dental floss 14 is received, and also defines ! another forwardly-located portion 12" having a smooth, curved lower outer surface 18 against which the exiting dental floss contacts during dispensing. Projecting from the upper surface of the first section is a single, upstanding floss-receiving post 20 provided with an upper through-hole or opening 20' through which is threaded the dental floss. The portion 12' has a smaller diametric extent than the portion 12" to define an annular shoulder 22 against which the end 16' of the housing section 16 abuts when the device 10 is fully assembled. The exterior diameter of the portion 12' is less than the interior diameter of the housing section 16, so that the housing section is partially telescopingly-mounted about the portion 12' in a manner that allows the thread to exit and be dispensed in the annular volume between the exterior surface of the portion 12' and the interior surface of the housing section 16, in the manner described herein below. The outer surface 18 of the forwardly-located portion 12" is provided with an elongated, longitudinally-extending groove or channel 24, as best seen in FIG. 14, in which runs the dental floss as it approaches the single post 20. As the dental floss is dispensed, or unwound from the supply reel 14, it exits from the open end of the interior portion 12', and travels along the groove 24 and passes through the opening 20' of the post 20. The depth of the groove 24 is such that the bottom section thereof is coextensive with the lower annular volume defined between the interior annular wall of the housing section 16 and the exterior surface of the section 12', so that the floss may pass unobstructed from the reel to the groove. There also may be provided a cutout on the end-edge 13 of the section 12 through which the floss may pass on its way to the groove 24, so that sharp turns and edges may be obviated in order to prevent the inadvertent cutting of the floss.

Figure 15:
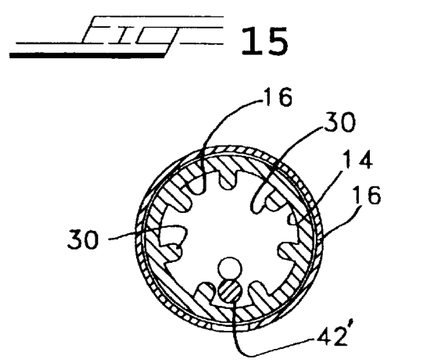
FIG. 15 is a cross-sectional view taken along line 7—7 of FIG. 12.

Mounted within the portion 12' is the dental floss supply or reel 14. This supply may be in reel or other form, and is preferably held therein to allow for rotational movement as the dental floss is dispensed. The reel 14 is a simple spool, or the like, about which the floss is wound, although other structures may be used, or just a simple ball of the floss may be used with a reel, as long as the ball is allowed adequate movement during dispensing. The reel 14 has a hollow interior and an annular end-flange 14'. The end-flange has a greater diametric extent than the main body of the reel or spool 14, which outer diameter is approximately equal to the inner diameter of the housing section 16, as best seen in FIG. 12, so as to provide a friction-fit between the outer surface of the end-flange 14' and the inner surface of the housing section 16. This force-fit allows the housing section to be retained in place when using the device, yet allows for easy opening of the device by sliding the housing section 16 away from the first section 12, in order to allow for replacing the reel 14. Other conventional structure may be used for achieving the releasable connection between the outer housing and the portion 12'. The reel 14 is provided interiorly thereof with a plurality of détentes or protuberances 30, there being, for example, seven such detents, as seen in FIG. 15, although more or less may be used, which together form a ratchet wheel. The detents 30 are equi-angularly spaced apart and project from the inner surface of the reel 14. The detents 30 are used to prevent rotation of the reel 14 when the device is being used to floss the teeth by means of a pawl mechanism 40 mounted in the interior of the housing section 16. The pawl-mechanism 16 is comprised of an elongated, resilient lever-arm 42 anchored to the interior of the housing section 16 by means of an anchor or post 44. The arm 42 may be made of resilient thermoplastic material, or other, well-known flexible material that allows the pivotal movement of the arm relative to the anchor 44. The lever-arm 42 extends a great enough distance parallel to the longitudinal axis of the housing section 16 to protrude into the interior of the reel 14, as seen in FIG. 12. Protruding from a mid-section of the lever-arm 42 is a button or dowel 46 that protrudes outwardly from the interior of the interior of the housing section 16 by means of a hole or opening 46' provided in the housing section. When the device 10 is being used to floss the teeth, the lever-arm is positioned as shown in FIG. 12, with the button 46 protruding fully outwardly through the hole 46', and with the end 42' of the lever-arm 42 being located between two adjoining detents 30 of the interior of the reel, as seen in FIG. 15, whereby rotation of the reel is prevented. When new floss is to be dispensed, one simply depresses the button 46 inwardly to force the lever-arm 42 more interiorly into the housing section, which thereby displaces the end 42' to a region that does not intersect with the detents 30, whereby free rotation of the reel is allowed in order to dispense the floss.

Figures 9, 11:
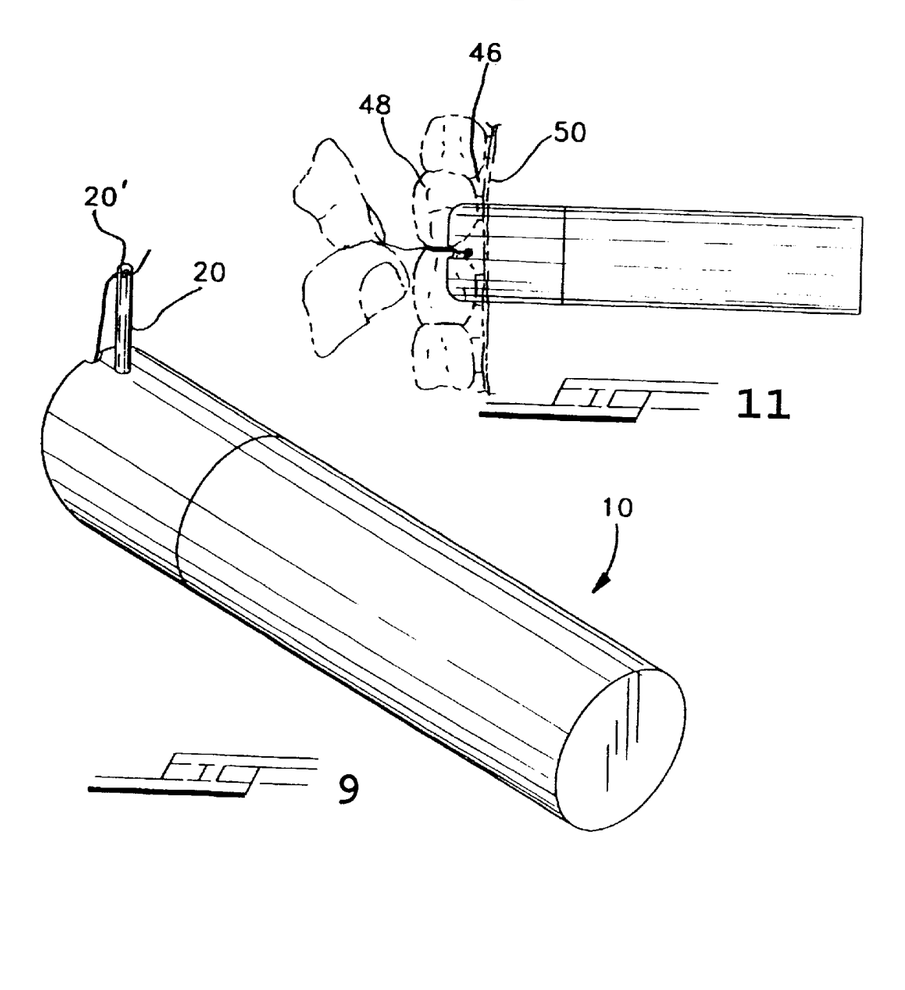
FIG. 9 is a perspective view of an embodiment of the present invention containing a strand of dental floss therein.
FIG. 11 is a top view of FIG. 10.
Figure 10:
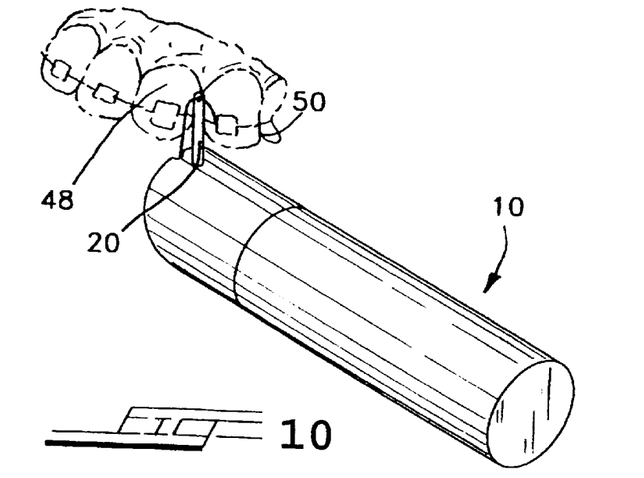
FIG. 10 is a perspective view thereof showing the single post of the dental flosser of an embodiment of the invention in use for flossing teeth.

FIGS. 10 and 11 show the device 10 in working position. The user is to grasp the loose end of floss with his finger. The floss support or post 20 can then be inserted into the clearance 46 between the teeth 48 and the arch wire 50. The dental floss is then intruded between the adjacent surfaces of the two teeth by alternating pressure between the two ends of the floss. Clean floss is easily dispensed during flossing by pressing the button 40. Since the end of the floss is held by the user, and not by another post as in the prior-art devices, the amount of tension applied to the floss may be varied at all times during the flossing. Furthermore, the end of the floss may be maneuvered to any desired orientation that more efficiently effects the flossing of the teeth, which the prior-art devices with two fixed, posts cannot achieve.

It is to be further recognized that the embodiments of the devices of FIGS. 8, 9–13, and 1–7, may be made of inexpensive disposable materials. In this manner, the device would provide an inexpensive flossing device that could be considered or sold as disposable. The devices may, on the other hand, be made of higher cost materials that would render it to expense to be considered disposable. It is to be further recognized that the embodiments of the devices; the present invention including these shown in FIGS. 8, 9–13, and 1–7 may be used for orthodontic applications, in particular, but without limitation, to be used by individuals that have braces or bridges. On the other had these devices can also be used in non-orthodontic related applications, in particular and without limitation, they may be used by individuals that do not have braces or bridges.

While this invention has been explained in relation to its preferred embodiment, it is to be understood the various modifications thereof will be apparent to those skilled in the art upon reading this specification. For example', the flosser can be used with or without the dispenser, and the locking dispenser shown an embodiment can be substituted with many known methods of securing floss including manual securing. In addition, the dental flosser and dispenser can be used in other applications other than orthodontic use. Therefore, it is to be understood that the invention disclosed herein is intended to cover all such modifications as shall fall within the scope of the appended claims.

What is claimed is:

1. A single post flossing device comprising:
   a. a body portion having a thickness and a length and having a first end and a second end;
   b. an intermediate housing portion having a thickness and a length and having a first end and a second end;
   c. a slender post portion having a thickness and a length and having a first end and a second end;
   d. a floss portion having a thickness and a length and having a first end and a second end;
   e. the second end of the body portion being attached to the first end of the intermediate housing portion, the first end of the slender post portion being attached to the intermediate housing, the first end of the floss portion being adjacent and fixed to the second end of the slender post portion, and the second end of the floss portion being free from attachment to the device; and,
   f. the thickness of at least part of the slender post portion being substantially thinner than the thickness of the body portion and the intermediate-housing portion.

2. The single post flossing device of claim 1, wherein the intermediate housing comprises a wall; an opening in the wall; a spool of floss; and the floss extending through the opening and being removably attached and fixed to the second end of the slender post porting.

3. The single post flossing device of claim 1, wherein the thickness of at least part of the slender post is not greater than about 5 mm.

4. The single-post flossing device of claim 1, wherein the thickness of at least part of the slender post is not greater than about 3 mm.

5. The single post flossing device of claim 1, wherein the intermediate housing portion is shaped to form a bend and the thickness of at least part of the slender post is not greater than about 1.5 mm.

6. A disposable single post flossing device comprising:
   a. a body portion having a thickness and a length and having a first end and a second end;
   b. a slender post portion having a thickness and a length and having a first end and a second end;
   c. a floss portion having a thickness and a length and having a first section and a second section;
   d. the second end of the body portion being rigidly attached to the first section of the slender post portion; the first end of the floss portion being permanently fixed to the second end of the slender post portion, and the second section of the floss portion being free from attachment to the device; and,
   e. the thickness of the slender post portion being thinner than the thickness of at least part of the body portion and the thickness of the slender post portion being thinner than about 5 mm.

7. The disposable single post flossing device of claim 6, wherein the slender post portion comprises a twisted wire strand; the twisted wire strand having a loop at the second section of the post; the first end of the floss being permanently fixed in the loop.

8. The disposable single post-flossing device of claim 6, wherein the first end portion of the slender post portion is removably attached to the body portion.

9. The disposable single post flossing device of claim 7, wherein the first end portion of the slender post is removably attached to the body portion.

10. A dental flossing device comprising:
   a. a main housing having a dental floss support portion, a handle portion, and a hollow interior for containing a reel of dental floss; interiorly therein;
   b. a reel of dental floss
   c. a disengageable locking mechanism for preventing the rotation of said dental floss reel; and,
   d. at least part of said reel having a substantially cylindrical shape and at least part of said hollow interior having a substantially cylindrical shape with a diametric extent larger than the diametric extent of said part of said reel, said reel being telescopingly mounted inside said hollow interior for allowing rotational motion to said reel when said locking mechanism is disengaged.

11. The dental flossing device of claim 10 wherein said reel of floss and said locking mechanism are mounted in the interior of said handle portion and wherein said handle portion is of a substantially hollow cylindrical shape for ease of grasping and economy of manufacture.

12. The dental flossing device of claim 10 wherein said locking mechanism comprises a ratchet, said ratchet comprising a cantilevered arm having a free end, said free end having a detent for engagement with at least one tooth, said cantilevered arm being movable for removing engagement of said detent with said at least one tooth in order to allow rotation of said reel for the dispensing thereof.

13. The dental flosser of claim 12 wherein said cantilevered arm has a protrubance; said main body comprises a wall and an opening in the wall; at least part of said protrubence protruding through said opening in the wall for allowing removing of said detent with said at least one tooth by means of manipulating said protrubance from outside said wall.

14. The dental flosser of claim 13, wherein said opening in the wall is in a section of said handle portion easily accessible by the fingers of the user while they are comfortably positioned for grasping said handle portion for flossing of the teeth whereby fresh floss can easily be dispensed during flossing by manipulation of said protuberance.

15. The dental flosser of claim 12, wherein said hollow interior has a forward section an intermediate section and a rear section, at least part of said reel is mounted in said forward section at least part of said at least one tooth is mounted in said intermediate section and at least part of said cantilevered arm is mounted in said rear section.

16. The dental flosser of claim 15, wherein at least part of said forward section said intermediate section and said rear section have a substantially cylindrical shape and at least part of said handle portion has a substantially cylindrical shape and wherein the cylindrical shape of said sections correspond to the cylindrical shape of said handle portion; whereby said handle portion can be molded in a shape most appropriate for the handling of the device and will not require enlarged portions to contain supplies of dental floss, large supplies can be stored within the dimensions of said handle utilizing the dimensional extent of the length of said handle and whereby the floss can be stored and dispensed from la section in close proximity to the support section without requiring an awkward enlargement of such a section.

17. A single post flossing device comprising:
  a. a handle portion having a thickness and a length and having a first end and a second end;
  b. an intermediate portion having a thickness and a length and having a first end and a second end;
  c. a slender post portion having a thickness and a length and having a first end and a second end;
  d. a floss portion having a thickness and a length and having a first section and a second section; and,
  e. the second end of the handle portion being attached to the first end of the intermediate body portion, the first end of the slender post portion being attached to the intermediate body portion, the first section of the floss portion being adjacent and fixed to the second end of the slender post portion and the second section of the floss portion being free from attachment to the device.

18. The single post flossing device of claim 17, wherein at least part of the post is thin enough to allow insertion of the post into a clearance between the teeth to be flossed and a fixed orthodontic appliance.

19. The single post flossing device of claim 18, wherein at least part of the post is thin enough to allow the user to maneuver the post portion inside the clearance between the teeth and a fixed orthodontic appliance.

20. The single post flossing device of claim 18, wherein at least part of the body portion protrudes in a direction perpendicular to the post.

21. The single post flossing device of claim 20 wherein at least part of the slender post is thin enough or of cylindrical shape in order to allow the user to rotate the post by laterally rotating the device in the clearance without obstruction from the fixed orthodontic appliance.

22. The single post flossing device of claim 17, wherein the slender post portion comprises a twisted wire strand having a loop at the second end of the post; the first end of the floss being adjacent and fixed to the loop.

23. The single post flossing device of claim 22, wherein the loop is wider than at least part of an intermediate section of the post thereby forming a thin post which is easy to maneuver and a widened loop which is easy to thread and gentle to the gums.

24. A method of flossing using a single support flossing device comprising:
  a. providing a length of floss having a first end and a second end, a support having a first end and a second end, a main body portion having a first end and a second end, and the first end of the support being fixed to the main body portion with at least a section of the main body portion protruding in a direction perpendicular to said support; and said first floss being fixed to said second of the support in a manner allowing the floss to be suspended in a plurality of direction;
  b. grasping said body portion in one hand;
  c. using the second hand to suspend the floss;
  d inserting the floss into the mouth;
  e. positioning the floss between the teeth;
  f. utilizing the length of the support to urge the floss upwardly between the teeth;
  g. rotating said body portion to a position most favorable to user and adjusting the position as necessary during the flossing of the teeth; and,
  h. tilting said support to urge the floss to clean the convex surface of the teeth.

25. A method of flossing using a single post flossing device for an individual having orthodontics comprising:
  a. providing a length of floss having a first end and a second end, a post having a first end and a second end and the first end of the floss being fixed to the second end of the post;
  b. inserting the second end of the post and a piece of attached floss into the clearance between the orthodontics and the teeth and gums and positioning the floss between the teeth;
  c. moving the floss, in a flossing action, along the teeth; and,
  d. maintaining the second end of the post portion in the space between the orthodontics and the teeth and gums during at least a portion of the flossing movement.

26. The method of claim 25 wherein step (d) includes the added steps of:
  (d-1) manipulating the post within the clearance in such a manner wherein the floss is urged to clean the convex surface of the teeth; and, (d-2) maintaining the second end of the post portion in the space between the orthodontics and the teeth and gums during at least a portion of the manipulating.

27. The method of claim 25, wherein step (a) includes the added step of fixing said second end of floss to a non-integral floss support and wherein said inserting the second end of the post is performed by the user using different hands to apply pressure to the opposite sides of the floss thereby allowing the user to easily control the extent of the insertion and thereby allowing the user to easily adjust the taughtness of the floss.

28. The method of claim 27, wherein step (d) includes the added steps of independently manipulating the floss supporting means on the opposite sides of the floss in such a manner wherein the floss is urged to clean the convex surfaces of the teeth and wherein the manipulation of the independent floss support is not restricted by the fixed floss.

29. The method of claim 25 wherein step (a) includes the added step of providing a handle portion having a first end and a second end, and the first end of said post being fixed to the second end of the handle portion, and at least part of the handle portion protruding in a direction perpendicular to the post; and wherein step (b) includes the added step of:

(b-1) laterally rotating the device to an orientation favorable to the user prior to insertion;

(b-2) adjusting the position of the device during the insertion to various orientations thereby facilitating an easy and accurate insertion of the post.

30. The method of claim 29, wherein step (d) includes the added steps of:

(d-1) manipulating the post within the clearance in such a manner wherein the floss is urged to clean the convex surfaces of the teeth;

(d-2) laterally rotating the device during the manipulation to various orientations favorable to the user, thereby facilitating easy and thorough cleaning of the convex surfaces of the teeth.

* * * * *